(12) United States Patent
Felix et al.

(10) Patent No.: US 7,175,612 B2
(45) Date of Patent: Feb. 13, 2007

(54) SUCTION LIMITING DEVICE WITH VARIABLE CONTROL

(75) Inventors: Augustus Felix, Cranston, RI (US); Kevin Ranucci, North Attleboro, MA (US); Karen E. Kullas, Taunton, MA (US); Adam P. Angell, Coventry, RI (US); Lisa Futato, Barrington, RI (US); Dan Hass, West Greenwich, RI (US)

(73) Assignee: C.R. Bard, Inc., Murray Hill, NJ (US)

(*) Notice: Subject to any disclaimer, the term of this patent is extended or adjusted under 35 U.S.C. 154(b) by 456 days.

(21) Appl. No.: 10/374,706

(22) Filed: Feb. 26, 2003

(65) Prior Publication Data

US 2004/0230169 A1 Nov. 18, 2004

(51) Int. Cl.
*A61M 1/00* (2006.01)
*F16K 24/00* (2006.01)
*F16K 5/10* (2006.01)

(52) U.S. Cl. .................. 604/323; 604/32; 604/35; 604/119; 604/129; 604/320; 604/45; 604/324; 137/215; 251/208

(58) Field of Classification Search ............ 604/32, 604/33, 35, 119, 129, 247, 320, 323, 9, 30, 604/45, 324; 137/215, 216, 216.1, 216.2, 137/217, 218, 416.1; 251/88, 188, 192, 208, 251/264, 304
See application file for complete search history.

(56) References Cited

U.S. PATENT DOCUMENTS

| | | | | |
|---|---|---|---|---|
| 4,383,935 A | * | 5/1983 | Hull | 261/78.1 |
| 4,997,006 A | * | 3/1991 | Zlobinsky et al. | 137/625.21 |
| 5,057,080 A | | 10/1991 | Takahashi | |
| 5,060,687 A | * | 10/1991 | Gayton | 137/218 |
| 5,226,885 A | | 7/1993 | Takahashi | |
| 5,299,561 A | | 4/1994 | Yoshimoto | |
| 5,401,255 A | | 3/1995 | Sutherland et al. | |
| 5,531,712 A | | 7/1996 | Malcolm et al. | |
| 5,547,456 A | | 8/1996 | Strobl et al. | |
| 5,564,457 A | * | 10/1996 | Beck | 137/15.06 |
| 5,575,424 A | * | 11/1996 | Fleischmann | 239/436 |
| 5,643,229 A | | 7/1997 | Sinaiko | |
| 5,730,727 A | * | 3/1998 | Russo | 604/118 |
| 5,807,238 A | | 9/1998 | Feldman et al. | |
| 5,830,214 A | | 11/1998 | Flom et al. | |
| 5,840,015 A | | 11/1998 | Ogino | |
| 6,070,582 A | * | 6/2000 | Kee | 128/207.16 |
| 6,095,971 A | | 8/2000 | Takahashi | |

(Continued)

*Primary Examiner*—Tatyana Zalukaeva
*Assistant Examiner*—Michael G. Bogart
(74) *Attorney, Agent, or Firm*—Darby & Darby

(57) ABSTRACT

A suction limiting device with variable control for use in a surgical system includes a main vent body having a fluid carrying bore extending therethrough and a variable vent mechanism having a main vent opening in selective fluid communication with the fluid carrying bore so as to permit introduction of atmospheric air into the fluid carrying bore. The vent mechanism being adjustable so that the degree of airflow into the fluid carrying bore is variable between a fully open position to a fully closed position where atmospheric air is prevented from entering the fluid carrying bore. The suction limiting device also includes a valve disposed within the main vent body and positionable between an open position when negative pressure and a closed position when positive pressure exists in the main vent body.

32 Claims, 9 Drawing Sheets

U.S. PATENT DOCUMENTS

| | | |
|---|---|---|
| 6,132,369 A | 10/2000 | Takahashi |
| 6,142,980 A | 11/2000 | Schalk |
| 6,254,061 B1 | 7/2001 | Levine et al. |
| 6,340,344 B1 | 1/2002 | Christopher |
| 6,447,473 B1 | 9/2002 | Levine et al. |
| 6,611,971 B1 * | 9/2003 | Antoniello et al. ............ 4/570 |
| 2001/0025160 A1 * | 9/2001 | Felix et al. .................. 604/183 |
| 2002/0103419 A1 | 8/2002 | Christopher |

* cited by examiner

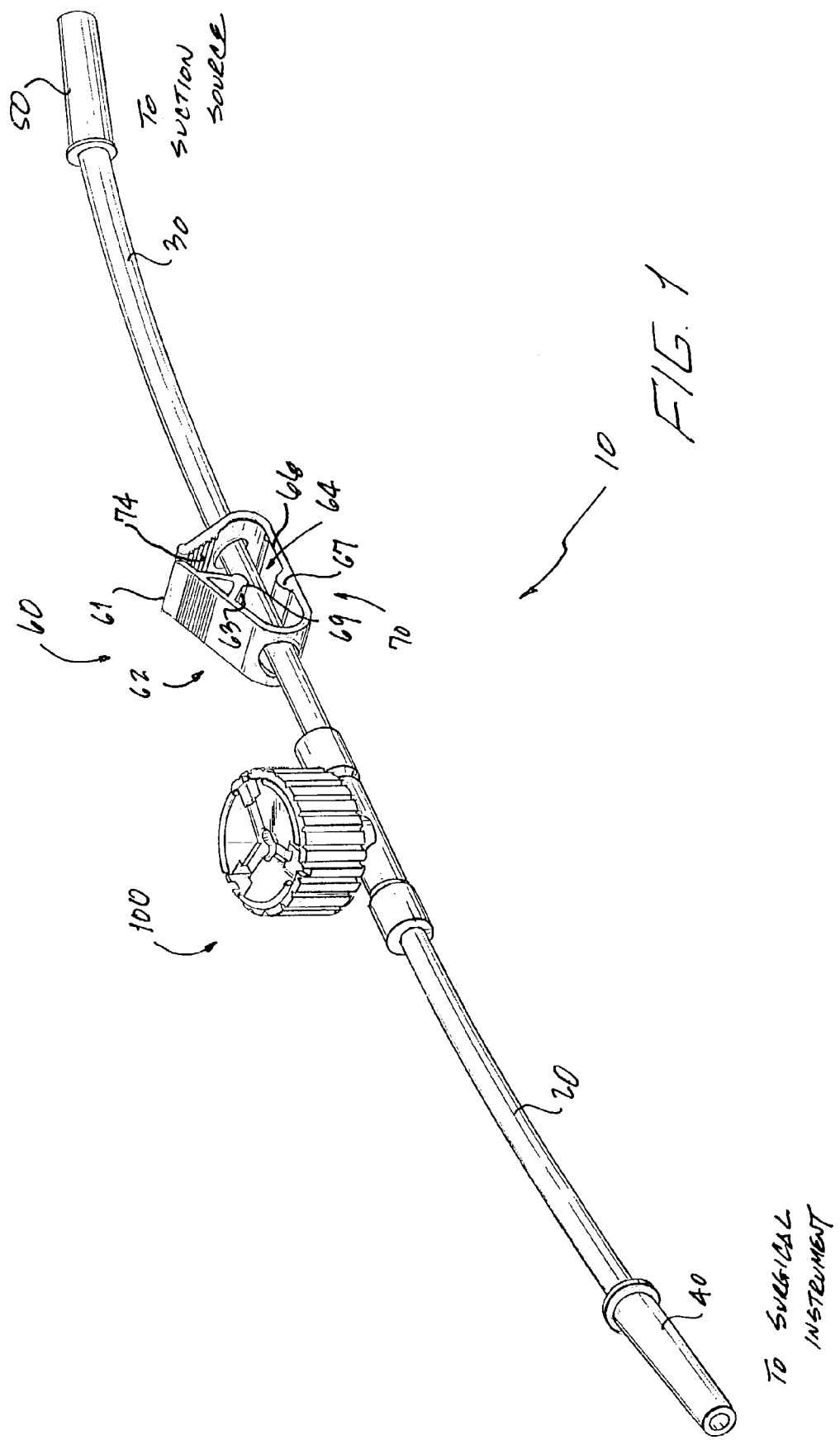

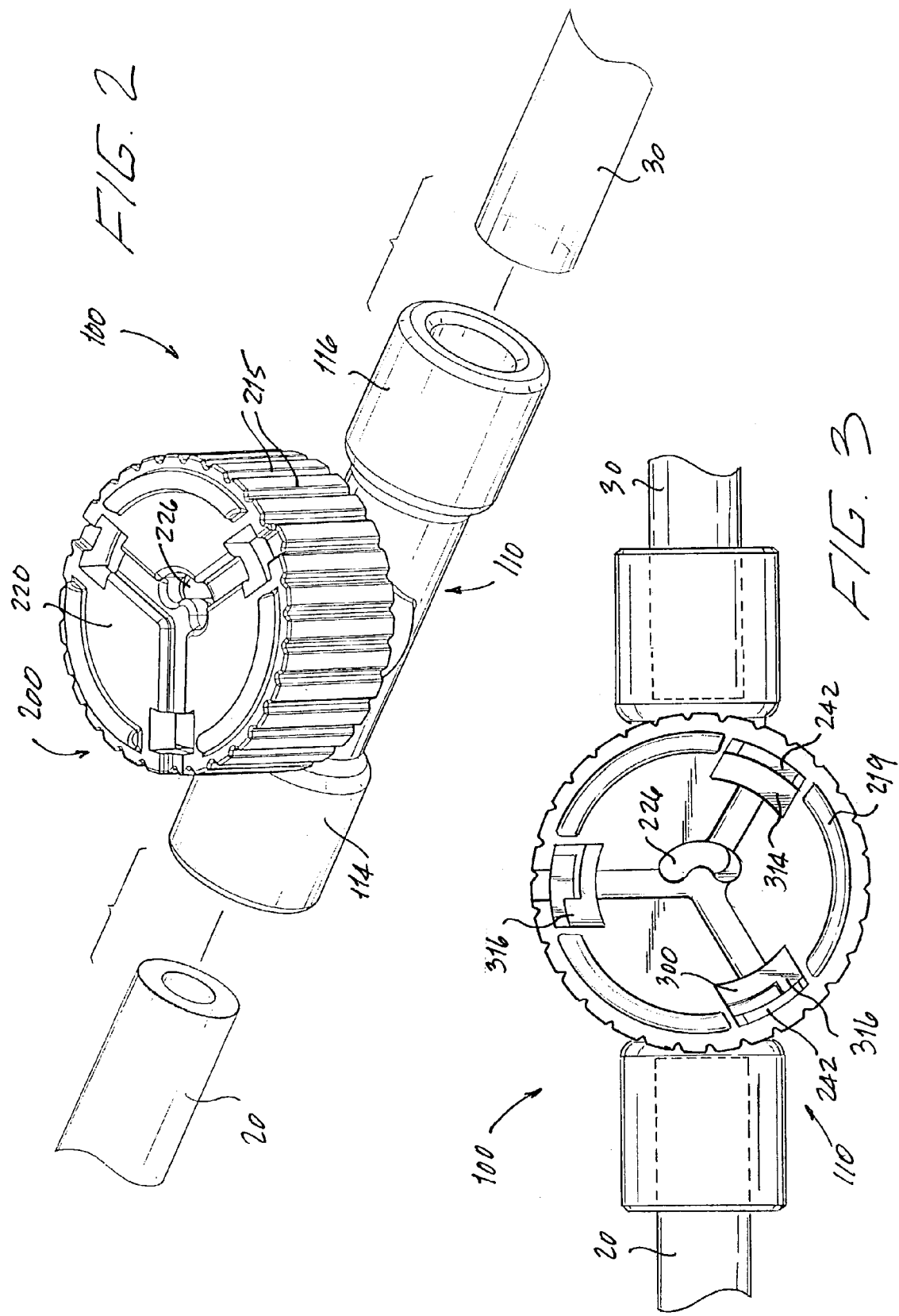

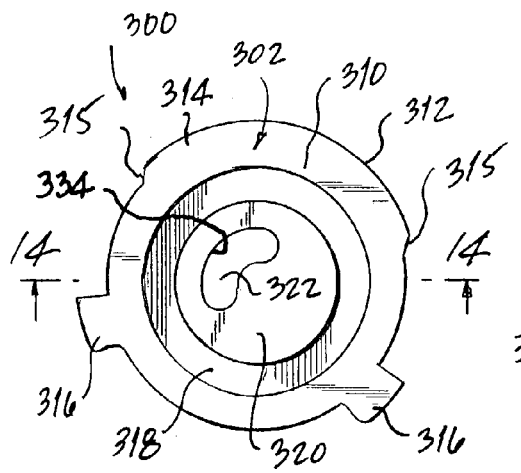
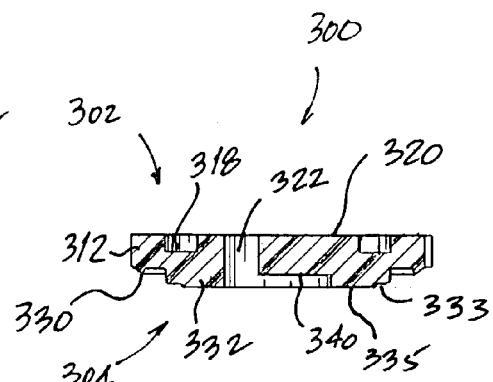
FIG. 13
FIG. 14
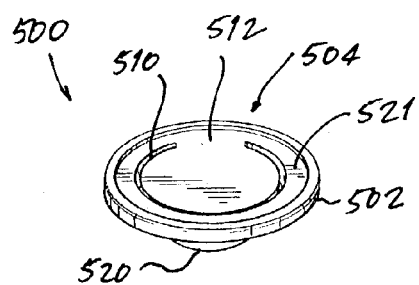
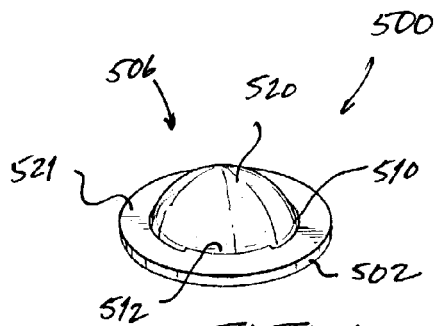
FIG. 15
FIG. 16
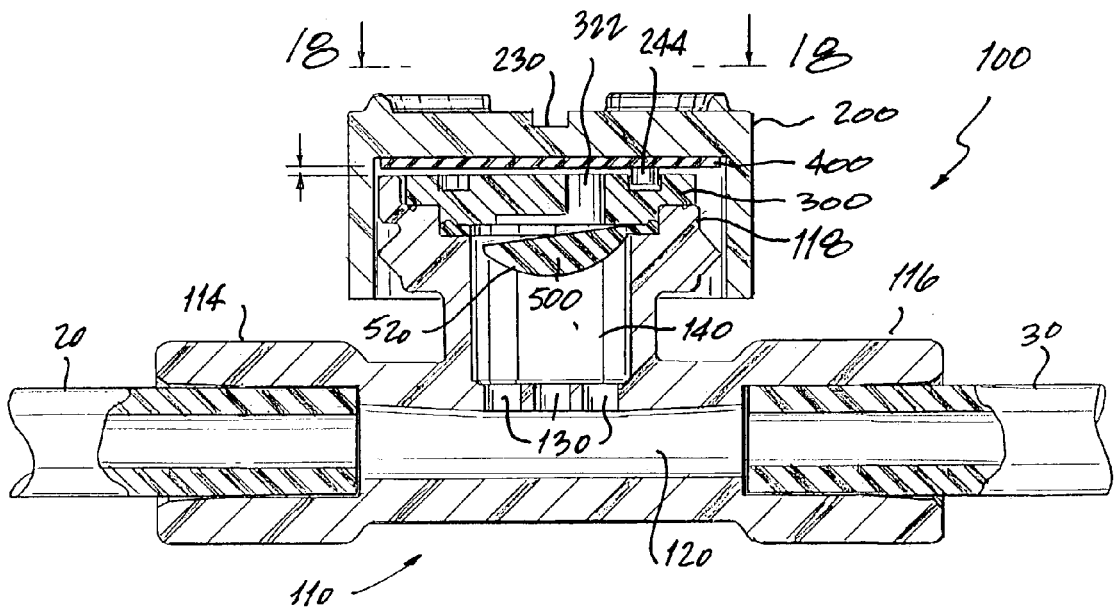
FIG. 17

SUCTION LIMITING DEVICE WITH VARIABLE CONTROL

TECHNICAL FIELD

The present invention relates generally to relief valves, and more particularly to a surgical suction device regulator which can be installed within a conduit that is connected to a vacuum source at one end and to a surgical device at the other end and is used to carry fluid from the operative site.

BACKGROUND

During the course of a surgical operation on a patient, it is often necessary to remove from the site of the operation various body fluids, tissue, and debris or fluids that have been injected. For example, a number of surgical operations utilize an irrigation inflow system which is used in the surgical operation, such as arthroscopic surgery, for providing irrigation fluid to the joint to distend the joint sufficiently to visualize and operate in the joint space arthroscopically, to provide sufficient pressure to tamponade internally any blood vessels compromised which may bleed, and also, to lavage the joint to remove debris.

During arthroscopic surgery, other devices are often utilized. These devices include an arthroscopic shaving system of which the shaving blade functions by rotating and cutting fragments of loose debris in the joint, and by providing a cannulated and integral means of removing this fragmented shaven debris. The shaver handpiece contains at its distal end, an attachment barb, that can be connected via suction tubing to the operating room's vacuum/suction system. In the process of removing this debris, the vacuum is activated and pulls the debris through the cannulated shaver blade and out of the joint space.

The vacuum system may be unregulated and the full effect of the vacuum can be applied to the joint via the suction tubing to the shaver blade. When this occurs, the pressure in the joint space may decrease. Depending upon the patient's condition and the capacity of the irrigation pump system, the resultant pressure in the joint space may or may not be sufficient to maintain distention and to tamponade any bleeding vessels. Oftentimes, the resultant pressure in the joint space decreases, as more fluid is withdrawn from the joint, than that which can be infused, thus creating a deficit. When the pressure in the joint decreases to below that of the exposed, compromised blood vessels, the vessels can potentially bleed.

It is therefore important that the proper level of negative pressure is applied to the suction line over the course of the surgical operation since inadequate or excessive negative pressure within the suction line can lead to complications. Over distention of the operative space is not desirable since it can lead to complications of a serious nature and therefore, the suction line is used to withdraw fluid, debris and the like from the operative space. Conversely, it is not desirable for the negative pressure in the suction line to become excessive since this leads to a different set of complications, namely, those noted above.

In order to prevent these complications from occurring, it has been found beneficial to install a relief valve between the vacuum source and the surgical device in order to control the amount of vacuum that is applied to the operative site. It is known to place a vent in the suction line so that the surgeon can limit the negative pressure within the suction line by opening the vent. In other words, such suction control usually consists of a valve that can be adjusted to admit a certain flow of ambient air into the suction line, thereby reducing the suction force at the surgical device. For example, in an arthroscopic operation, the suction line is connected between a vacuum source and the shaving device. During the arthroscopic operation, the surgeon will activate the suction line to withdraw fluid and debris away from the operation site through the suction line and use the vent or valve mechanism to effectively maintain the desired amount of negative pressure within the suction line.

There are a number of valve mechanisms available for venting the suction line. For example, in some suction devices, the air intake of the regulating valve is controlled by the position of the surgeon's finger over the air intake. Unfortunately, this type of device is very cumbersome to operate since it requires the surgeon to place and maintain his or her finger over the air intake. If the surgeon's finger should be become slightly displaced as by a slipping action or the device itself slips, then the air intake is opened and ambient air rushes through the valve and into the device. This results in the suction being reduced or completely interrupted.

Many of the other types of valve mechanisms that are used are of an "on/off" type. In other words, the vent is either fully opened or fully closed. The disadvantage with this type of arrangement is that it does not offer the variability that is often desired in venting the negative pressure (suction force) in the suction line. In other words, the optimum venting might be a condition between the "on" position and the "off" position of the vent.

An adjustable type valve is generally disclosed in U.S. Pat. No. 5,531,712 to Malcolm et al. In this patent, a relief valve for regulating the suction of an endoscope includes a plunger which can be screwed into a fluid escape channel. At one end thereof, the plunger includes a conical tip that is shaped and dimensioned to progressively obstruct an escape port, in combination with longitudinal grooves along the threaded walls of the plunger. Thus, the patent only teaches adjusting the air flow through the escape port by adjusting the plunger. There is no teaching or suggestion of incorporating a second valve element to be used with the plunger to further provide variability of the valve.

It is therefore desirable to provide a relief valve mechanism that not only vents the suction line to ambient air under prescribed conditions but also has a mechanism that controls the vent in view of negative and positive pressure build ups in the suction line.

SUMMARY

A suction limiting device with variable control for use in a surgical system is provided and includes a main vent body having a fluid carrying bore extending therethrough from a first end to a second end and a variable vent mechanism having a main vent opening in selective fluid communication with the fluid carrying bore so as to permit introduction of atmospheric air into the fluid carrying bore. The vent mechanism being adjustable so that the degree of airflow into the fluid carrying bore is variable between a fully open position to a fully closed position where atmospheric air is prevented from entering the fluid carrying bore. The suction limiting device also includes a valve disposed within the main vent body and positionable between an open position when negative pressure exists in the main vent body and a closed position when positive pressure exists in the main vent body, wherein the closed position, the valve prevents fluid flow from the fluid carrying bore out of the vent mechanism.

In another aspect, a method of variable venting of a suction line in a surgical system that includes a suction limiting device that has a safety valve and is operatively connected to a vacuum source and a surgical instrument is disclosed. The method includes the steps of activating the vacuum source so that the suction limiting device is under negative pressure and this results in the valve being urged opened. The venting is accomplished by introducing a variable amount of atmospheric air into the surgical device/field for reducing the negative pressure that is applied to the suction limiting device by rotation of a switch that forms a part of the vacuum limiting device. The switch is positionable between a closed position where atmospheric air is prevented from entering the suction limiting device and a fully open position where a main vent opening of the suction limiting device is opened a maximum amount to permit atmospheric air to flow therethrough. The valve is closed when positive pressure within the suction limiting device exceeds a prescribed amount, wherein in the closed position, the valve prevents fluid flow through the main vent opening.

The present device and method are intended to be placed in line within the suction tubing after the shaver handpiece or other surgical instrument and before the suction line runs off the sterile field to the vacuum canister. The present device is designed to limit the outflow fluid flow and thus maintain joint pressure and distention and also, simultaneously, provides a device that when used in a closed system will allow the maximum pressure generated by the irrigation system to be transferred to the joint, without leakage through the proposed device. The device will limit the outflow fluid flow by relieving the full vacuum effect allowed to be transferred to the joint. This in turn will reduce the amount of irrigation fluid used in a surgical operation and thus reduce the number of change-overs of irrigation bags and/or suction collection vessels.

Further aspects and features of the exemplary apparatus disclosed herein can be appreciated from the appended Figures and accompanying written description.

BRIEF DESCRIPTION OF THE DRAWINGS

The invention will be more fully understood by reference to the following drawings which are for illustrative purposes only:

FIG. 1 is a perspective of a suction line assembly;

FIG. 2 is a perspective view of an adjustable vent device for use in the assembly of FIG. 1 and shown relative to a pair of suction lines that are exploded therefrom;

FIG. 3 is a top plan view of the adjustable vent device of FIG. 2;

FIG. 13 is a top plan view of a cap for use in the adjustable vent device of FIG. 2;

FIG. 14 is a cross-sectional view taken along the line 14—14 of FIG. 13;

FIG. 15 is a top perspective view of a valve for use in the adjustable vent device of FIG. 2;

FIG. 16 is a bottom perspective view of the valve;

FIG. 17 is a cross-sectional view of the view of the adjustable vent device connected to a pair of suction lines in a rest position;

DETAILED DESCRIPTION OF THE PREFERRED EMBODIMENTS

Figure 4:
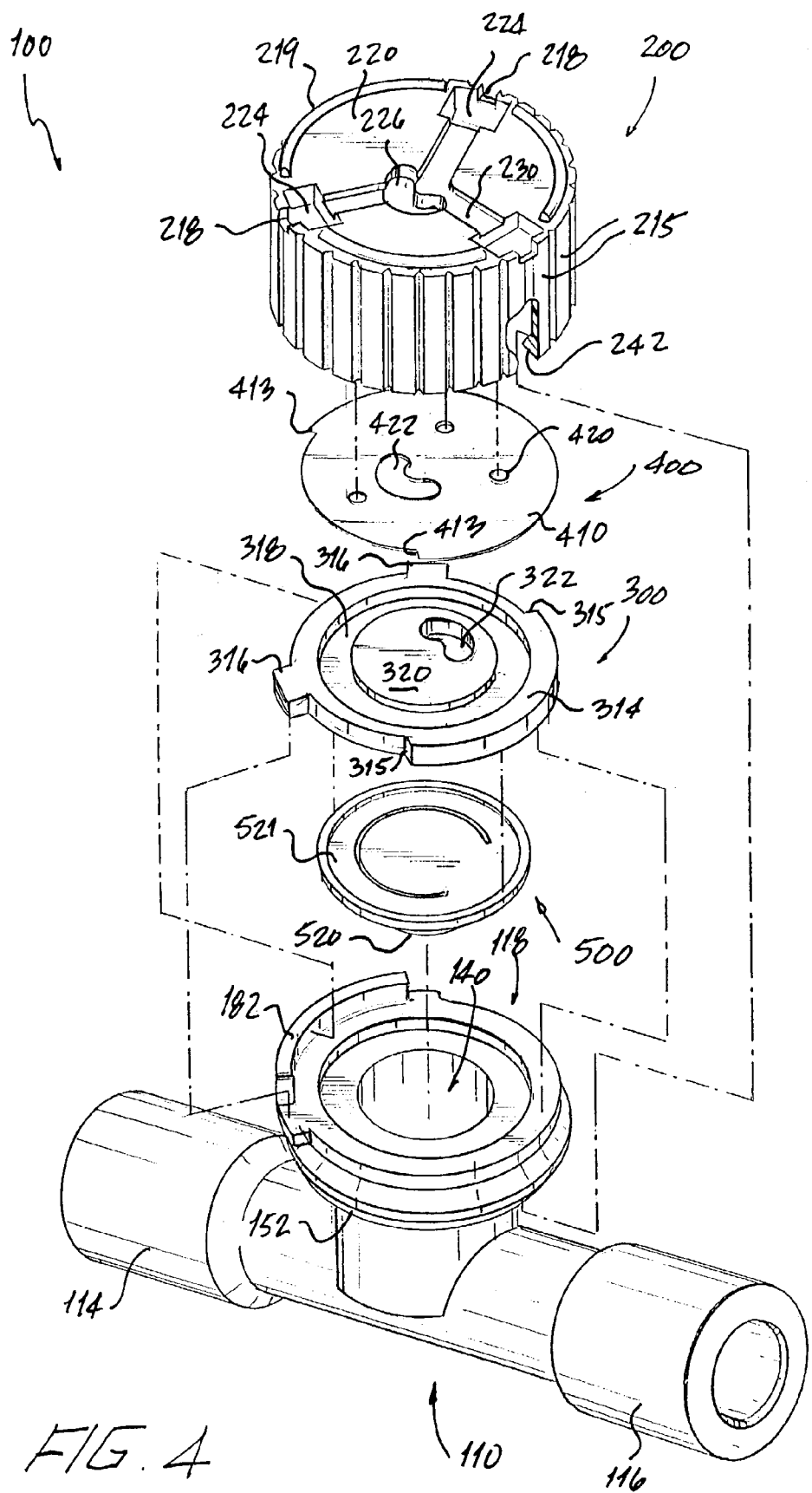
FIG. 4 is an exploded perspective view of the adjustable vent device of FIG. 2.
Figure 5:
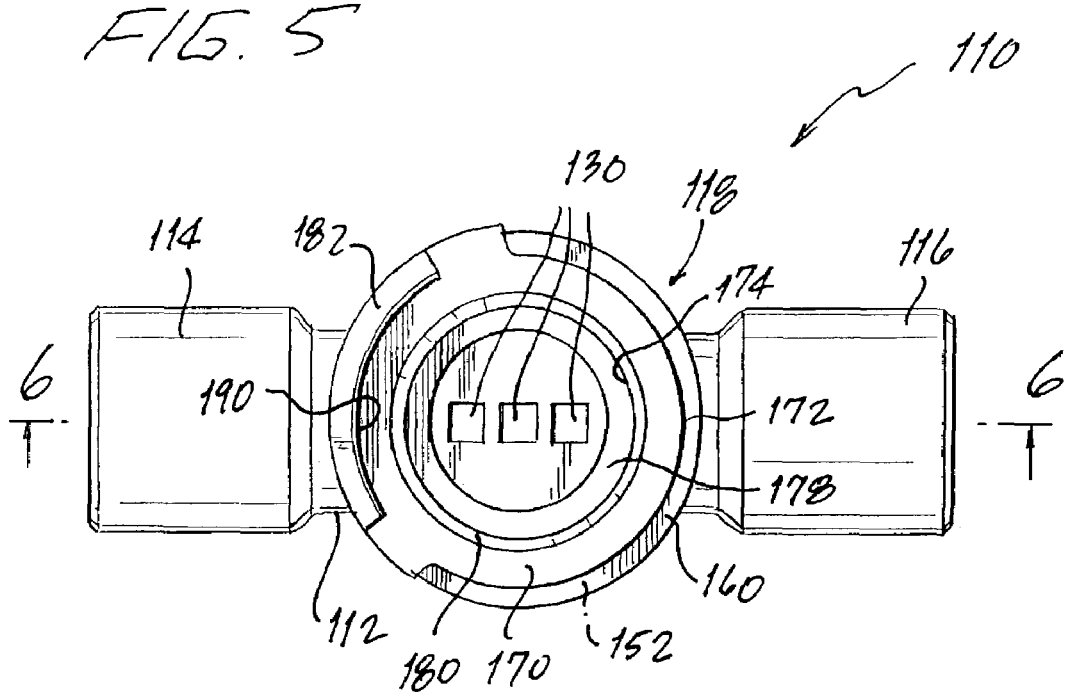
FIG. 5 is a top plan view of a main vent body of the adjustable vent device of FIG. 2.
Figure 6:
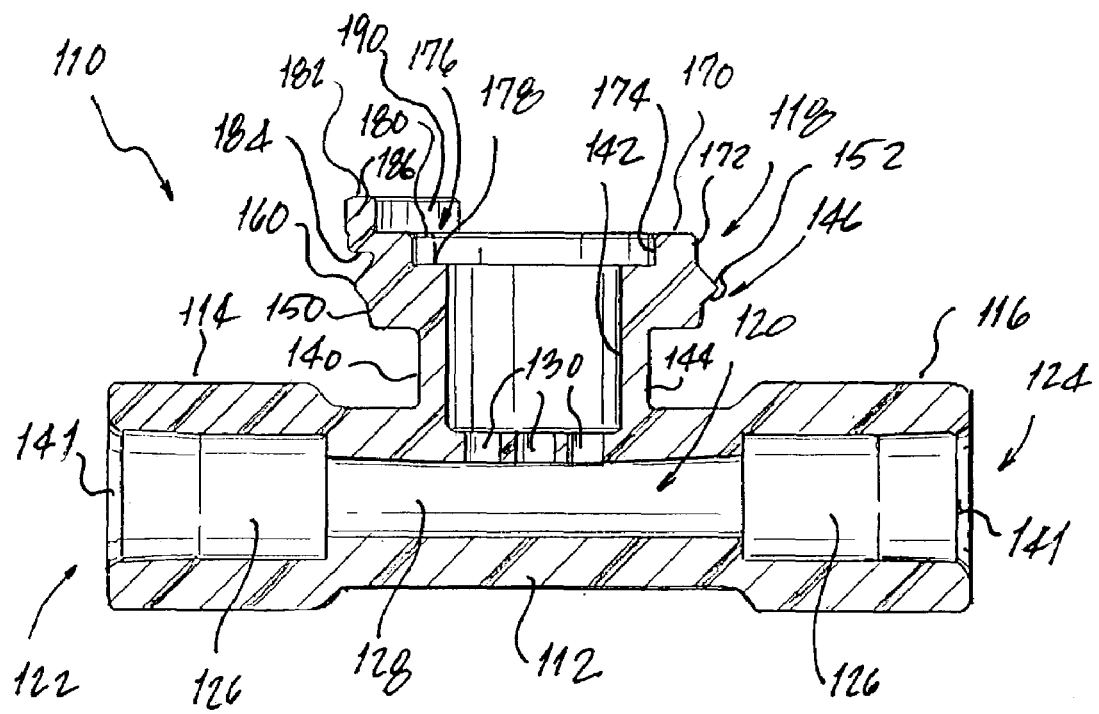
FIG. 6 is a cross-sectional view taken along the line 6—6 of FIG. 5.
Figure 7:
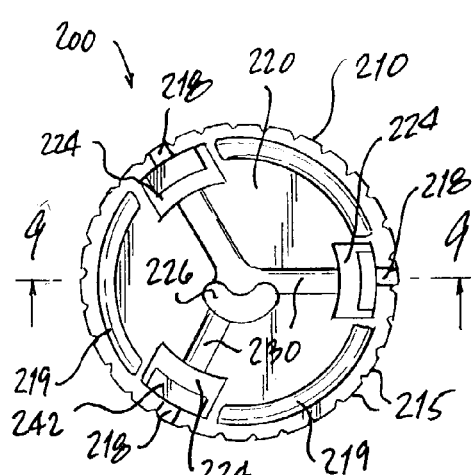
FIG. 7 is a top plan view of a switch for use in the adjustable vent device of FIG. 2.
Figure 8:
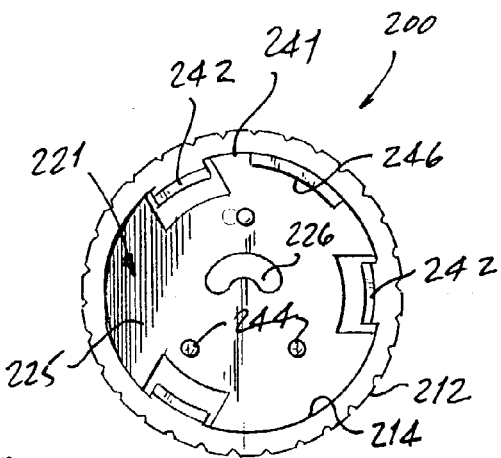
FIG. 8 is a bottom plan view of the switch of FIG. 6.
Figure 9:
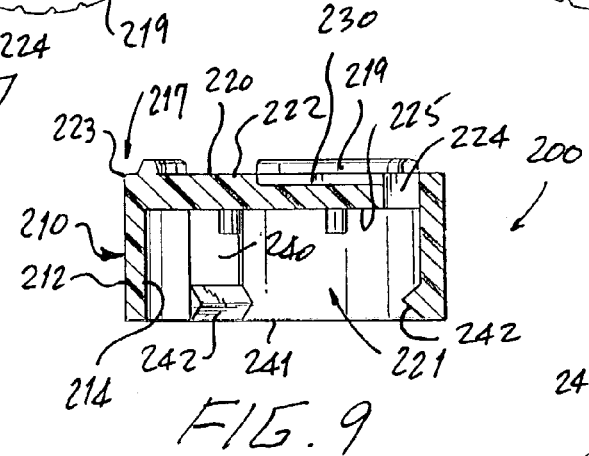
FIG. 9 is a cross-sectional view taken along the line 9—9 of FIG. 7.

Referring first to FIG. 1, a suction line assembly 10 including a suction limiting device with variable control 100 ("the adjustable vent device") according to one exemplary embodiment is illustrated. The suction line assembly 10 includes a first suction line section 20 that is fluidly coupled to one end of the adjustable vent device 100 and a second suction line section 30 that is fluidly coupled to the other end of the adjustable vent device 100. The first and second suction line sections 20, 30 can be formed of any number of suitable materials and in one embodiment, the suction lines sections 20, 30 are tubular members formed of a plastic material that can have different elastic make-ups depending upon the application. For example, one suitable material for the suction lines sections 20, 30 is polyvinylchloride. The lengths of each of the first and second suction lines 20, 30 is also variable depending upon the precise application. At an end of the first suction line section 20 opposite the adjustable vent device 100, a connector 40 is provided and is sealingly coupled thereto. Similarly, at an end of the second suction line section 30 opposite the adjustable vent device 100, a connector 50 is provided and is sealingly coupled thereto. The connectors 40, 50 can be selected from any number of commercially available fluid conduit connectors. For example, the illustrated connectors 40, 50 are tubular plastic connectors (e.g., polyvinylchloride) that sealingly mate with the first and second suction section lines 20, 30, respectively, at one end thereof, while the opposite end of each mates with another component. More specifically, the connector 40 is intended to mate with a suction line port of a surgical device (not shown), such as an arthroscopic shaver handpiece or the like, and the connector 50 is intended to mate with a vacuum/suction system (not shown).

Preferably, the suction line assembly 100 also includes a pinch clamp 60 of a conventional design. The pinch clamp 60 is formed as a single part and has a first flexible arm 62 and a second flexible arm 70 that is spaced therefrom and constructed to interlocking mate therewith so as to securely capture the second suction line 30 within a space 64 formed between the first flexible arm 62 and a base section 66 that is formed between the first and second flexible arms 62, 70. The space 64 is defined between a section of a triangular shaped projection 63 that extends from the first flexible arm 62 and a nub or bump 67 that is formed on the base section 66. At its apex, the triangular shaped projection 63 has a rounded end 69 that seats against the bump 67 to enclose the space 64, thereby capturing the second suction line 30 therein.

The first and second flexible arms 62, 70 are constructed so that they are of a ratcheting type in that the first flexible arm 62 has a pointed tip 61 that interlockingly mates between adjacent teeth 74 that are formed as part of an array of teeth 74 formed on an inner surface of the second flexible arm 70. To reduce the space 64, the first flexible arm 62 is ratcheted down with respect to the teeth 74 and as this occurs, the second suction line 30 is pinched by the triangular shaped projection 63 so that it becomes partially occluded. In other words, the fluid flow rate through the second suction line 30 in the region of the pinch clamp 60 is restricted. To increase the fluid flow rate, the flexible arms 62, 70 are adjusted so that the first flexible arm 62 is ratcheted upward toward the end of the second flexible arm 70, thereby increasing the area of the space 64.

Referring to FIGS. 2–16, the adjustable vent device 100 is actually formed of a number of different parts that are assembled together. More specifically, the adjustable vent device 100 includes a main vent body 110, a rotatable switch 200, a cap 300, a gasket 400, and a valve 500 that are assembled together as described below.

The main vent body 110 is preferably an integrally formed plastic (e.g., acrylic) piece. The main vent body 110 has an elongated tubular section 112 that has a first section 114 (leg) and an opposing second section 116 (leg) with a vent housing 118 being disposed therebetween and is in indirect fluid communication with the first and second sections 114, 116. More specifically, the elongated tubular section 112 has a bore 120 that extends completely therethrough from one end 122 (associated with the first section 114) to an opposite end 124 (associated with the second section 116). The bore 120 does not have a uniform diameter from the first end 122 to the second end 124 in that, according to one exemplary embodiment, the bore 120 has end sections 126 and an intermediate section 128 therebetween. Preferably, the diameters of the end sections 126 are the same; however, the diameter of the intermediate section 128 is less than the diameter of the end sections 126. Preferably, a chamfer 141 is formed at each of the ends 122, 124 and more specifically, the distal ends of the end sections 126 have the chamfer 141 formed thereat. The chamfer 141 is tapered outwardly so that the immediate distal ends have a greater diameter than the other sections of each of the end sections 126. This is to receive the ends of the suction lines 20, 30.

One suitable material for forming the main vent body is CYROLITE®, which is an impact modified, acrylic-based multipolymer compound for molding and extrusion that is commercially available from CYRO Industries, Rockaway, N.J. However, this is merely one exemplary material and many others are suitable.

The vent housing 118 is an integral part of the main vent body 110 and extends outwardly from the intermediate section 128 and is in indirect fluid communication with the intermediate section 128 through one or more ports 130 that are formed in the tubular wall of the intermediate section 128. For example, each port 130 can be in the form of a shaped opening that provides communication between an interior of the intermediate section 128 and an interior of the vent housing 118. In the illustrated embodiment, there are three ports 130 with each port 130 being square shaped and spaced slightly apart from an adjacent port 130. It will be appreciated that the number of ports 130 and the shape and size of the ports 130 can vary from application to application. The total area of the ports 130 should not be less than the area of main vent opening 322.

The vent housing 118 has a cylindrical base 140 that is integrally attached at one end to the intermediate section 128 such that each port 130 opens into a cavity defined by the cylindrical wall that defines the base 140. The cylindrical base 140 has an inner surface 142 and an outer surface 144 and it extends to an upper end 146. The vent housing 118 also includes a number of features formed at or near the upper end 146 of the cylindrical base 140 for coupling the switch 200 and receiving other parts of the assembly. More specifically, first and second annular flanges 150, 160, respectively, are integrally attached to the outer surface 144 of the cylindrical base 140. The first and second flanges 150, 160 are formed adjacent one another such that an a first annular shoulder 152 is formed therebetween. The first annular flange 150 is formed closer to the main vent body 110 and the diameter of the first annular flange 150 is less than a diameter of the second annular flange 160. This results in the second annular flange 160 protruding beyond the first annular flange 150 and the first annular shoulder 152 defines a guide surface as will be described hereinafter.

The vent housing 118 also includes a ring structure 170 that is integrally formed above the first annular flange 150. The diameter of the ring structure 170 is less than the diameter of the first annular flange 150 and more specifically, the diameter of the ring structure 170 is about equal to the diameter of the second annular flange 160. Accordingly, from the side, the first annular flange 150 protrudes radially beyond both the ring structure 170 and the second annular flange 160. From the side view, it will be appreciated that the ring structure 170 has two beveled surfaces that converge at a point which defines the outermost diameter of the ring structure 170. The ring structure 170 has an outer peripheral surface 172 and an inner surface 174 and an upper planar surface 176 that extends between the surfaces 172, 174. The diameter of the inner surface 174 is greater than the diameter of the inner surface 142 of the cylindrical base 140 and therefore a ledge 178 is formed therebetween. A second annular shoulder 180 is formed between the ledge 178 and the inner surface 174.

The ring structure 170 also has a flange element 182 that extends partially around a circumferential length thereof. More specifically, the flange element 182 is integrally attached to the outer peripheral surface 172 and protrudes outwardly therefrom. An upper surface of the flange element 182 lies flush with the upper planar surface 176 of the ring structure 170. In one exemplary embodiment, the flange element 182 is arcuate shaped and extends less than 180 degrees around the outer surface 172. In the illustrated embodiment, the flange element 182 increases the diameter of the ring structure 170 in the region where the flange element 182 is formed such that the outer diameter of the ring structure 170 and the flange element 182 is approximately equal to the outer diameter of the second annular flange 160. Because the flange element 182 extends beyond the outer surface 174, a shoulder or notch (thread) 184 is formed between the flange element 182 and a corresponding section of the second annular flange 160.

The vent housing 118 also includes a raised vertical wall or rail 186 that is integrally formed with the flange element 182 around a section thereof. In one exemplary embodiment, the rail 186 is a vertical wall that has a square or rectangular cross-section and is formed on an upper surface of the flange element 182. The rail 186 therefore has an arcuate shape (e.g., crescent shaped) and according to one exemplary embodiment, the rail 186 does not extend the complete length of the flange element 182 and further the width of the rail 186 is about equal to the width of the flange element 182 so that the annular upper surface 176 of the ring-structure 170 is not impinged upon by the rail 186. Thus, an arcuate shoulder 190 is formed between the upper surface 176 and the rail 186.

The rotatable switch 200 is generally in the form of a cap that is constructed to be rotatably mated with the main vent body 110. The switch 200 includes a vertical peripheral wall 210 that is integrally attached to a cover wall 220 at a peripheral outer edge 223 and at one end thereof so that the switch 200 generally is in the form of a cap that has a cavity 221 defined by the walls 210, 220. The peripheral wall 210 is a cylindrical wall that has an outer surface 212 and an inner surface 214. The outer surface 212 preferably has gripping features 215 formed thereon to facilitate the gripping and rotation of the switch 200. In one exemplary embodiment, a plurality of vertical ribs 215 are formed as part of the outer surface 212. The ribs 215 provide a roughened surface that is easier for the user to grasp when it is desired for the user to rotate the switch 200 to change its position relative to the main vent body 110 as will be described hereinafter. At an upper end 217 of the ribs 215 in selected locations, a plurality of notches 218 are formed. Each notch 218 is formed across the width of one rib 216 such that the adjacent ribs 216 protrude above the rib 216 that has a reduced height due to the notch 218 being formed. In one exemplary embodiment, there are three notches 218 formed in the switch 200, with the notches 218 preferably being equidistant from each other. These notches are a continuation of a plurality of recessed channels 230.

The cover wall 220 has an outer surface 222 and an opposing inner surface 225 that faces the inner surface 214 of the cylindrical wall 210. The outer surface 222 has a number of features formed therein to permit proper venting of the main vent body 110. More specifically, the outer surface 222 has a main opening 226 formed therethrough and optionally, the outer surface 222 has a plurality of first openings 224 formed therethrough that are created by pins in a mold that forms the tabs 242 and are provided to reduce the complexity and cost of the mold. The main opening 226 provides communication between the ambient atmosphere around the switch 200 and the cavity 221. In the exemplary embodiment, there are three spaced first openings 224 formed in the cover wall 220 and each opening 224 has a substantially rectangular shape with one edge bordering the peripheral edge of the cover wall 220. The openings 224 are aligned with the notches 218 so that each notch 218 opens into one of the openings 224. Between next adjacent openings 224, an arcuate rib 219 is formed on the outer surface 222 at or near the peripheral edge of the cover wall 220. Thus, there are three arcuate ribs 219 formed as part of the illustrated cover wall 220. The arcuate ribs 219 provide clearance between the main vent opening 226 and a surgical surface, such as a surgical drape, when the device is inadvertently inverted. The switch 200 design also minimizes the likelihood of accidental shut-off of the adjustable vent device 100 during use.

According to one exemplary embodiment, the main opening 226 is formed slightly off set from the center of the cover wall 220 and it is generally formed in the shape of a kidney. The main opening 226 serves as a vent port of the switch 200. The kidney shape of the main opening 226 and its location close to the center point of the switch 200 serve to yield more angular displacement with each unit of rotation of the switch 200.

The outer surface 222 of the cover wall 220 further includes a plurality of recessed channels 230 formed therein and more specifically, each channel 230 connects one of the notches 218 (edge openings) with the main opening 226. The channels 230 are linear in construction with one end thereof forming an entrance into the notch 218 and the other end thereof forming an entrance into the main opening 226. In other words, the channel 230 is axially aligned with one corresponding notch 218 and in this embodiment, the depths of the channels 230 and the notches 218 are about equal. The channel 230 is also axially aligned with one first opening 224; however, this is because this is a preferred location to form such openings due to the pins in the molding process. Because the notches 218 are circumferentially spaced from one another, the channels 230 generally represent grooves that are formed in the cover wall 220 and converge toward one another near or at the main opening 226. These notches 218 and the channels 230 form secondary vent pathways relative to the main opening 226 for allowing atmospherically air to enter the adjustable vent device 100 (the main vent body 110) through a different or secondary path in the event that that the main vent hole (the main opening 226) is occluded accidentally or inadvertently. These channels 230 run from the outer edge of the switch 200 to the vent port (main opening 226) and the precise number of channels 230 can be varied to allow for the necessary area of airflow. It will also be appreciated that the tops of these channels 230 is preferably covered with a label 600, protective cover, or the like (FIG. 21) which prevents an object (such as a surgical drape) from being accidentally pulled into one or more of the channels 230, thereby resulting in blocked airflow. The label 600 effectively creates the secondary pathways since it forms the ceiling or top of the pathways that are open only at their ends (at the notch 218 and main opening 226) as will be discussed in greater detail in reference to FIG. 21. In sum, the switch 200 does not have to have the secondary channels 230 and therefore, in one alternative embodiment, the switch 200 only has the main vent opening 226 formed therein.

The inner surface 214 of the cylindrical wall 210 has a plurality of slightly recessed tracks 240 formed therein along a substantial length of the cylindrical wall 210. Each track 240 is formed relative to one first opening 224 and the width of the track 240 is preferably about equal to the width of the first opening 224. In other words, the track 240 is in communication with one first opening 224. The inner surface 214 also includes a plurality of tabs 242 that are formed circumferentially therearound and more specifically, each tab 242 is formed within one of the tracks 240 at a lower edge 241 of the cylindrical wall 210. One exemplary tab 242 has a triangular cross-section with the apex of the triangular tab 242 facing inwardly with respect to the inner surface 214. Each tab 242 therefore has a pair of beveled surfaces (cam surfaces) that converge to the apex. Once again, it will be appreciated that the tracks 240 and tabs 242 result from the preferred mold construction (e.g., from the molding tools, etc.)

Inner surface 225 of the cover wall 220 also has a plurality of posts 244 that extend outwardly therefrom. The posts 244 can be arranged in a number of different arrangements and in the exemplary embodiment, the posts 244 are arranged in a triangular manner. A stop 246 is also provided within the cavity 221 and more specifically, the stop 246 has a vertical base section 248 that seats against the inner surface 225 of the cover wall 220 and extends along a section of the inner surface 214 of the cylindrical wall 210. The stop 246 has a beveled section 249 that contacts and is integral with the inner surface 214 of the cylindrical wall 210. The stop 246 is slightly curved since it is integral with the inner surface 214 of the cylindrical wall 210, which is curved itself. The stop 246 is formed between two of the first openings 224.

Preferably, the switch 200, including all of its features, is formed as a single integral part. Any number of semi-flexible materials can be used to form the switch 200 and preferably, the switch 200 is formed of a semi-flexible plastic material, such as polypropylene. The semi-flexible properties are desirable to permit the switch 200 to flex when it is press-fit onto the valve body.

In another embodiment, the switch 200 has seal beads integrally formed as part of the underside of the switch 200. The switch 200 is preferably formed in the embodiment of a semi-flexible material, such as LDPE (linear low density polyethylene) or polypropylene. The seal beads, when under compression against an outer face of the cap 300, closes a main vent opening of the cap 300 from atmospheric air. Both seals beads are placed on the underside of the switch 200 with an interior seal bead being positioned around a perimeter of the vent opening 226 in the switch 200 and an exterior seal bead, which is annular in shape, is positioned toward the outer edge of the underside of the switch 200.

FIGS. 4 and 13–14 illustrate an exemplary cap 300 in greater detail. The cap 300 is a rigid member that is preferably formed of a suitable plastic material, such as CYROLITE®, or it can be formed of the same material as the main vent body 110 to facilitate ultrasonic welding (between identical materials). The cap 300 is constructed and contoured to mate with the main vent body 110 such that it seals the vent housing 118. The cap 300 therefore has an outer face 302 and an inner face 304 that faces the vent housing 118. The cap 300 has a body 310 that is generally circular in shape with the exception of several features that slightly protrude from a peripheral edge 312 of the body 310. More specifically, the body 310 has a slight peripheral flange 314 formed around a section of the peripheral edge 312 of the body 310 and also a pair of integral locating and restraining tabs 316 that are formed as part of the body 310 for restricting movement of the cap 300 when it is disposed on top of the vent housing 118. The tabs 316 are spaced a prescribed distance from one another so that when the cap 300 mates with the vent housing 118, the rail 186 is received between the tabs 316 such that the tabs 316 seats against the ends of the rail 186.

The tabs 316 are spaced from one another and have a generally square or rectangular shape. The tabs 316 are preferably dimensioned so that when the cap 300 mates with the vent housing 118, the tabs 316 do not extend beyond the rail 186 or only slightly extend therebeyond. In other words, it is desired for the distal edge of the tabs 316 and the outer surface of the rail 186 to be relatively flush with one another. The tabs 316 prevent rotation of the cap 300 about the vent housing 118 since the raised rail 186 is disposed between the tabs 316 and therefore, the raised rail 186 prevents rotation of the cap 300 since attempted rotation of the cap 300 in either direction causes one of the tabs 316 to abut one end of the rail 186, which thereby prevents rotation of the cap 300 and in turn align the main vent opening 322 with main opening 226 of the switch 200 which may be permanently adhered to the vent housing 118. The length of each tab 316 is preferably about equal to a distance defined between one end of the rail 186 and the corresponding end of the flange element 182. As a result, when the cap 300 mates with the vent housing 118, the tabs 316 seat against the end of the rail 186 at one end thereof, while the other end is preferably aligned with the end of the flange element 182.

The peripheral flange 314 is integral with the body 310 and serves to slightly increase the width of the body 310 along a section of the peripheral edge thereof. When the cap 300 is mated with the vent housing 118, the peripheral flange 314 slightly protrudes beyond the ring structure 170. Moreover, each end of the peripheral flange 314 preferably includes a chamfer 315. This is to create friction between the stop 246 of the switch 200 and the peripheral flange 314. This friction is created to minimize the accidental closing of the switch 200 if "bumped" during use.

The outer face 302 has a recessed ring or annular track 318 formed therein with a circular platform 320 being defined in the center of the annular track 318. The circular platform 320 is solid with the exception that it includes an opening 322 formed therein. The opening 322 is preferably identical in shape and dimensions to the second opening 226 and therefore, in the illustrated embodiment, the opening 322 has a kidney shape that extends completely through the body 310. This opening 322 serves as the main vent opening of the system.

The inner face 304 of the cap 300 also includes a number of features. More specifically, the inner face 304 has a number of concentric features that complement the construction of the vent housing 118. The inner face 304 has a first raised ring 330 that is formed along an outermost peripheral section of the inner face 304. Inside of the first raised ring 330, there is a raised platform 332 that is shaped and dimensioned so that it is received between the ring structure 170. The illustrated platform 332 therefore has a circular shape so that is can be received within the circular opening defined by the ring structure 170. The raised platform 332 is constructed so that there are actually two annular sections, namely one annular section 333 that is integrally attached to the body 310 and another annular section 335 that is integral with the annular section 333. The height of the annular section 335 is very small and therefore, the annular section 335 does not protrude that far beyond the inner face of the annular section 333. A recessed platform 340 is defined within the central opening of the annular section 335. The kidney shaped opening 322 that extends completely through the body 310 is formed between the annular section 335 with none of the structures obscuring the opening 322.

It will be appreciated that the annular section 333 is received within the ring structure 170 and therefore the opening 322 is in communication with and forms an entrance into the cavity defined by the cylindrical wall 140. The cap 300 can only be placed on the vent housing 118 in one way since the raised platform 332 is only received within the ring structure 170 when the cap 300 is orientated so that the rail 186 is received between the tabs 316 and the peripheral flange 314 is opposite the rail 186.

Figure 10:
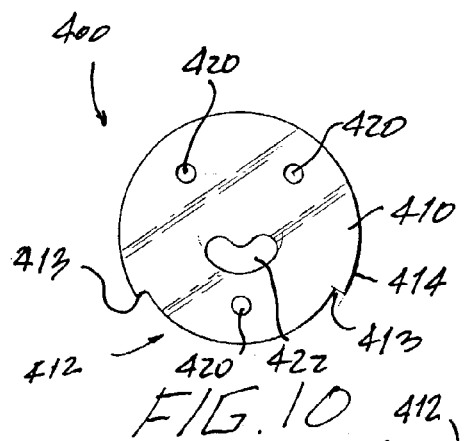
FIG. 10 is top plan view of a gasket for use in the adjustable vent device of FIG. 2.
Figure 11:
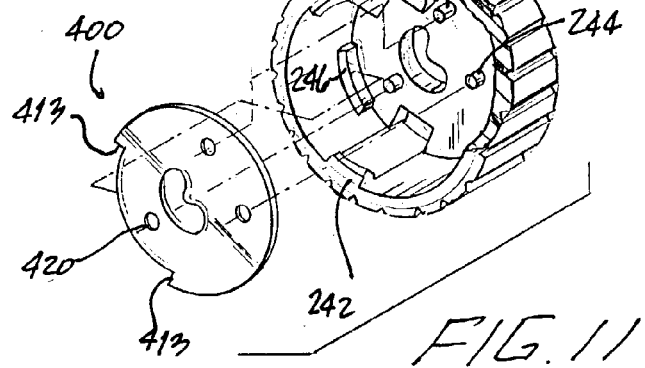
FIG. 11 is an exploded perspective view of the gasket and the switch illustrating the mating relationship between the two.
Figure 12:
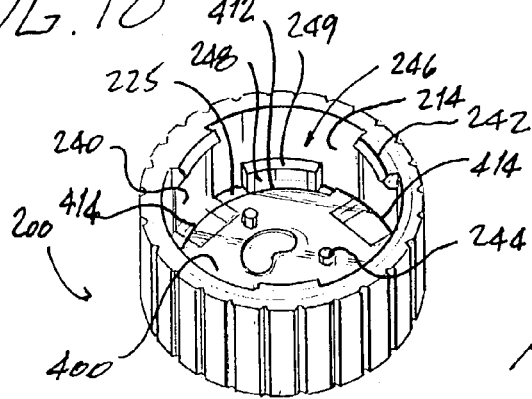
FIG. 12 is a perspective view of the gasket mated with the switch.

FIGS. 10–12 illustrate an exemplary gasket 400 in greater detail. The gasket 400 is a flexible member that is formed of a material that permits it to have the desired sealing and flexibility characteristics. For example, the gasket 400 can be formed of a rubber or elastomeric material, and in one exemplary embodiment, the gasket 400 is formed of silicone rubber (e.g., a silicone rubber 60 Durometer Shore "A" commercially available from Dow Chemical, Midland, Mich.). When this material is used, the gasket 400 has a transparent quality.

The gasket 400 is for reception between the switch 200 and the cap 300 when the adjustable vent device 100 is assembled. The gasket 400 has a body 410 that is substantially circular in shape with the exception that there is a peripheral cut-out 412 that extends along a circumferential length of the body 410 at its outer edge 414 thereof. The cut-out 412 terminates at two edges 413 that define respective shoulders with respect to the other sections of the body 410. The cut out 412 corresponds to the stop 246 of the switch 200. The body 410 also has a plurality of first openings 420 formed therein and at least one opening 422. The number of first openings 420 is equal to the number of posts 244 and moreover, the shape and dimensions of the openings 420 are complementary to the posts 244 so that the posts 244 are received through the openings 420 preferably with clearance. Accordingly, the illustrated openings 420 are circular shaped. The opening 422 has a shape and is dimensioned to be complementary to the opening 226 and more specifically, the openings 422, 226 are preferably identical is shape and size so that when the gasket 400 is positioned relative to the switch 200, the openings 422, 226 align and overlie one another. Thus, the illustrated opening 422 has a kidney shape.

The first openings 420 are formed through the body 410 so that the relative arrangement thereof is complementary to the arrangement of the posts 244. In the illustrated embodiment, the first openings 420 are arranged in a triangular pattern with one of the first openings 420 facing the cut-out 412. The opening 422 is formed generally between the first openings 420 (e.g., within the boundary of the imaginary triangle).

When the adjustable vent device 100 is assembled, the gasket 400 is fitted to the inner surface 225 of the cover wall 220 by aligning the first openings 420 with the posts 244 and then extending the posts 244 therethrough so that the gasket 400 lies flush against the inner surface 225. In this arrangement, the openings 422, 226 align and overlie one another and the outer edge 414 extends at least substantially to the inner surface 214 of the cylindrical wall 210 except in the region where the cut-out 412 is formed. In this arrangement, the gasket 400 covers the three openings 224 in varying amounts. It will be understood that in other embodiments, the first opening 224 can be covered more or less by the gasket 400. The outer edge of the gasket 400 within the cut-out region 412 is disposed near or at the vertical base section 248 of the stop 246.

FIGS. 4 and 15–16 illustrate one exemplary valve 500 in detail. The valve 500 can be any number of different types of valves that are constructed to performed the intended function. For example, valve 500 can be a flapper valve or an umbrella valve. For purpose of illustration only, the valve 500 in the Figures is shown as a flapper type valve. The flapper valve 500 has a number of characteristics that make it a good choice for the intended application. For example, the flapper valve 500 is a robust valve that is notable used in high debris situations, such as sanitary sewage applications and in toilets. The flapper valve 500 also possesses a relatively large sealing area, such that it may open and close readily, with minimum inertial force to overcome its seal. With some valves with small closure areas, debris could lodge readily in the seal area and further, with some valves, the small closure area may require some inertial force to overcome to open, when a vacuum is applied. The valve 500 should also posses a large opening (as in flapper and umbrella type valves) to enable it to open substantially, for two reasons, namely, noise mitigation (e.g., low whistling effect) and so that it is non-restrictive to air flow.

The illustrated flapper valve 500 is formed of resilient material, such as silicone rubber, and has an outer peripheral edge 502 that has a circular shape. The valve 500 has a first face 504 and an opposing second face 506 with the first face 504 being substantially planar when the valve 500 is in the completely closed position. The valve 500 has a slit 510 formed therein to define a valve body 520. The slit 510 is arcuate in nature and is almost circular in shape with the exception that the ends of the slit 510 terminate prior to joining one another in order to define a hinge 512 that connects the valve body 520 to the surrounding sections of the valve 500. Because the slit 510 is generally circular in nature, the valve body 520 has a generally circular outer edge, with the exception of the hinge 512, and the body section 521 that surrounds the valve body 520 across the slit 510 is generally in the form of a ring that surrounds the valve body 520. While the valve body 520 at the first face 504 is planar, the second face 506 thereof has a convex surface such that in the closed position, the convex portion of the valve body protrudes above the surrounding second face of the ring body section 521.

The valve 500 is sized so that it can be received within the vent housing 118 and more specifically, the valve 500 is disposed on the ledge 178 with the convex surface of the valve body 520 being disposed within the cavity defined by the cylindrical wall 140. The ring body section 521 has a width that is about equal to the width of the ledge 178 and this permits the valve body 520 to be disposed between the cylindrical wall 140 (e.g., over the entrance into the cavity defined by the cylindrical wall 140) to permit the valve body 520 to be drawn into this cavity when negative pressure (a suction force) is applied in the main vent body 110 as will be described hereinafter. The center of the valve body 520 is preferably also the center of the valve 500.

The assembly and operation of the adjustable vent device 100 are now described. The adjustable vent device 100 can be assembled in a number of different sequential steps and therefore, the following assembly steps are merely exemplary and not limiting. The main vent body 110 is positioned upright and the valve 500 is disposed into the vent housing 118 by orientating the convex surface of the valve body 520 so that it faces the vent housing 118 and then inserting this convex valve body 520 into the cavity defined by the cylindrical wall 140. The ring body section 521 seats on the ledge 178. When the valve 500 seats within the vent housing 118, the first face 504 is disposed below the upper planar surface 176. The exact location of the hinge 512 relative to the vent housing 118 is not critical since the convex valve body 520 is disposed within the cavity regardless of the position of the hinge 512.

The cap 300 is then disposed and attached to the body 110 (e.g., by ultrasonic welding) over the valve 500 and onto the vent housing 118. When ultrasonic welding is used, a hermetic seal is formed between the cap 300 and the body 110. More specifically, the cap 300 is orientated so that tabs 316 are disposed adjacent the ends of the rail 186 and the inner face 304 faces the valve 500. The cap 300 is then disposed on the vent housing 118 so that the annular section 333 is received within the ring structure 170 above the valve 500. The annular section 333 can even apply a slight force against the first face 504 of the valve 500. The opening 322 formed in the platform 320 of the cap 300 is disposed above the valve 500 so that the opening 322 provides fluid communication through the valve 500 to the cavity defined in the vent housing 118. The outer surface 334 of the opening 322 should be located closer to the center of the vent than the outer edge of the valve body 520.

The switch 200 and the gasket 400 are coupled to one another by disposing the posts 244 through the first openings 420 so that the gasket 400 seats against the inner surface 225 of the cover wall 220. Because the thickness of the gasket 400 is less than the length of the posts 244, the gasket 400 is permitted to travel up and down ("float") the posts 244 as will be described hereinafter. The gasket 400 thus does not have to seat against the inner surface 225 of the cover wall 220 and in fact, the gasket 400 will often be displaced therefrom during normal use of the adjustable vent device 100.

The switch 200 is then rotatably coupled to the main vent body 110 by positioning the switch 200 so that the stop 246 is disposed between the free ends of the tabs 316 of the cap 300. In other words, the stop 246 is not positioned in a location that corresponds to where the rail 186 is formed. The switch 200 is pressed down against the main vent body 110 until a snap fit results therebetween due to the tabs 242 engaging and snap-fittingly being received within the first annular shoulder 152 formed between the first and second flanges 150, 160. The beveled surfaces of the tabs 242 therefore act as cam surfaces and facilitate the snap-fit interlocking between the switch 200 and the main vent body 110 and also permit the switch 200 to be removed from the main vent body 110 by simply applying a force to the underside of the switch 200 in a direction away from the main vent body 110, thereby causing the tabs 242 to disengage from the first annular shoulder 152 (resulting in the switch 200 being free from the main vent body 110).

The tabs 242 ride within the first annular shoulder 152 as the switch 200 is rotated. Thus, the switch 200 is coupled to the main vent body 110 and more specifically, the vent housing 118 thereof so that it can rotate a prescribed degree relative to the vent housing 118. The tabs 316 (free ends thereof) restrict the degree of rotation of the switch 200 relative to the vent housing 118 since the tabs 246 engage one of the free ends of the tabs 316 as the switch 200 is rotated in one direction relative to the vent housing 118. Thus, one tab 316 acts as a first stop for restricting the rotation of the switch 200 in a first direction when one end of the stop 246 contacts the one tab 316, while the other tab 316 acts as a second stop for restricting the rotation of the switch 200 in a second direction when the other end of the stop 246 contacts the other tab 316.

It will be appreciated that the cap 300 is stationary and does not move and therefore, the opening 322 remains in a fixed position. This opening 322 serves as the main vent port of the adjustable vent device 100 since it provides the only communication with or entrance into the vent housing 118.

In fact, the first and second stops are positioned so that when the switch 200 is rotated to the first stop, the switch 200 is in a fully opened position since the second opening 226 (the kidney shaped opening) aligns with the vent opening 322 (complementary kidney shape) formed in the cap 300. In other words, the two vent openings 226, 322 at least substantially and preferably completely overlie one another so that atmospheric air can fluidly travel through the openings 226, 322 to the valve 500 where it then is permitted to flow into the interior of the vent housing 118 when the valve 500 is open. When the switch 200 is rotated to the second stop, the switch is in a fully closed position since the second opening 226 is not aligned with the vent opening 322 (i.e., the openings 226 and 322 are off set from one another), thereby preventing atmospheric air from freely flowing into the main vent body 110 as will be described hereinafter. The kidney shape of the openings 226, 322 permit the vent opening 226 of the switch 200 to provide partial airflow when the vent opening 226 is partially closed by the cap 300.

The adjustable vent device 100 is first installed in the assembly 10 by disposing the first suction line section 20 into the end section 126 at the first end 122 by solvent bonding the first suction line section 20 in the bore 120 and similarly, the second suction line section 30 is disposed into the end section 126 at the second end 124 by solvent bonding the second suction line section 30 in the bore 120. The connector 40 is frictionally fit on the other end of the first suction line section 20 and is intended to be mated with a complementary feature (e.g., an attachment barb) that is part of the surgical device (e.g., the shaver handpiece) (not shown). The other connector 50 is solvent bonding on the other end of the second suction line section 30 and is intended to be mated with a complementary feature that is part of the vacuum/suction system (not shown). The device 100 is placed more proximal to the vacuum than typical devices to relieve the full effect of vacuum on the patient.

The adjustable vent device 100 offers improved performance and more variability than similar devices found in the prior art. In the present system, the user has variable control over the main vent opening 322 due to the adjustable vent device 100 incorporating in the design of the vent opening 322 a variable diameter, which allows for greater flexibility to the surgeon and allows for optimum use depending upon source suction levels, shaver size (inner diameter) and inflow characteristics. This is accomplished by incorporating a floating gasket 400 between the switch 200 and the main vent opening 322. As previously mentioned, the vent opening 422 formed in the gasket 400 is always in the same position as the vent opening 226 of the switch 200. The purpose of the posts 244 is two fold. One purpose is to allow for alignment of the vent openings 422, 226 of the gasket 400 and the switch 200, respectively. The other purpose is to capture the gasket 400. The gasket 400 is captured by the posts 244 that in turn engage onto the annular track 318 that is formed in the outer face 302 of the cap 300 when the switch 200 interlockingly engages the main vent body 110. The annular nature of the track 318 permits radial movement of the posts 244 during rotation of the switch 200 during normal use of the adjustable vent device 100. There is a space formed between the gasket 400 and the outer face 302 of the cap 300 that allows the gasket 400 to float in the vertical direction along the posts 244. As will be described in greater detail below, when suction is applied to the main vent body 110, the gasket 400 is pulled downward over the main vent opening 322 formed in the cap 300 to create a seal along the entire length of the main vent opening 322. This, in turn, allows the vent device 100 to be variable. The posts 244 also serve to drive the gasket 400 as the switch 200 is rotated, thereby keeping the alignment of the gasket 400 and the main vent opening 322 maintained.

Figure 18:
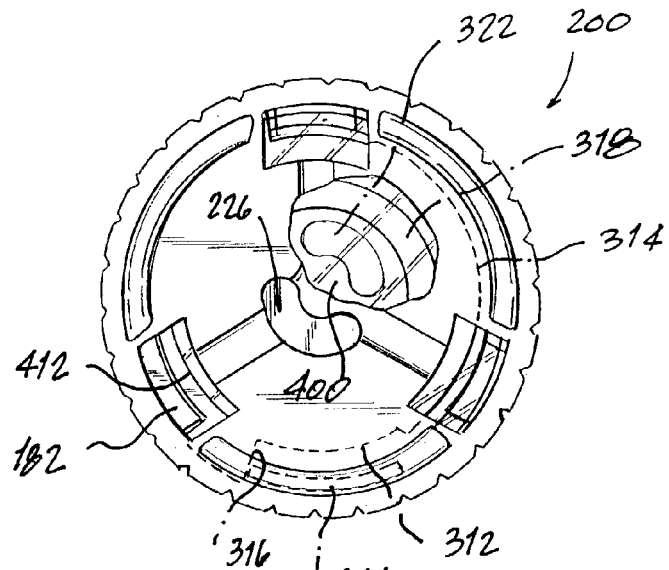
FIG. 18 is a top plan view, partially broken away, illustrating the adjustable vent device in a closed position.
Figure 19:
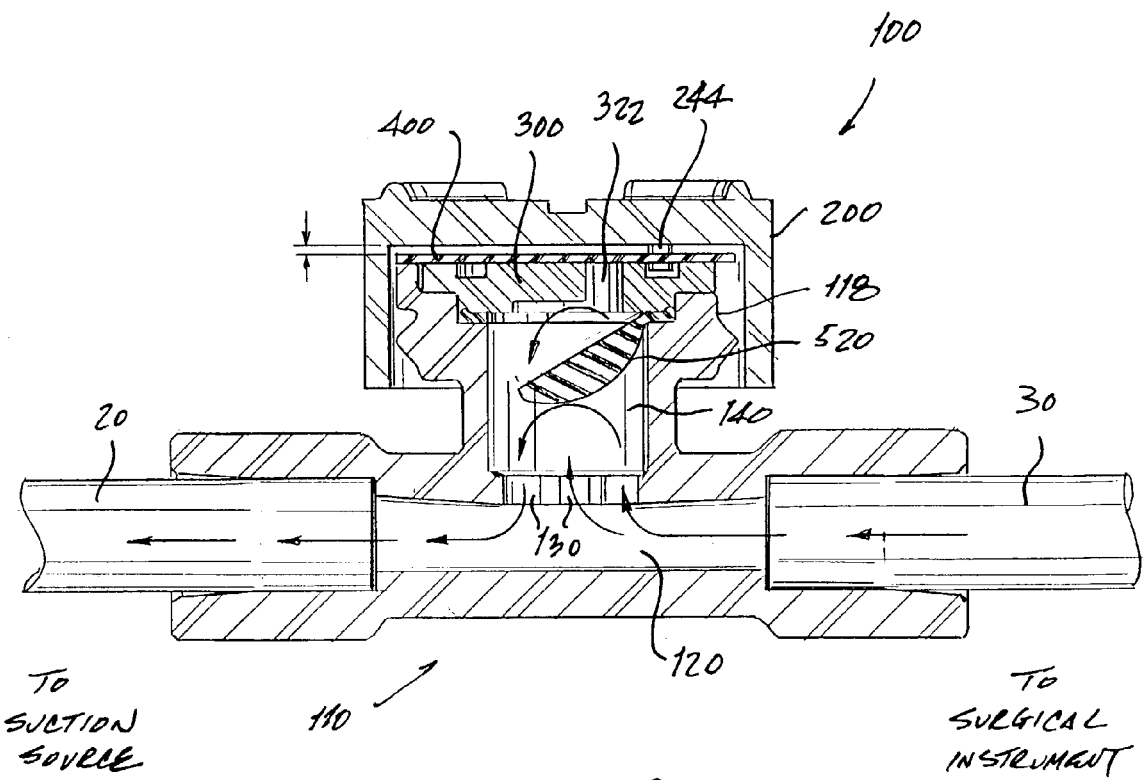
FIG. 19 is a cross-sectional view taken along the line 19—19 of FIG. 3 illustrating the valve in an open position when the system is actuated.
Figure 20:
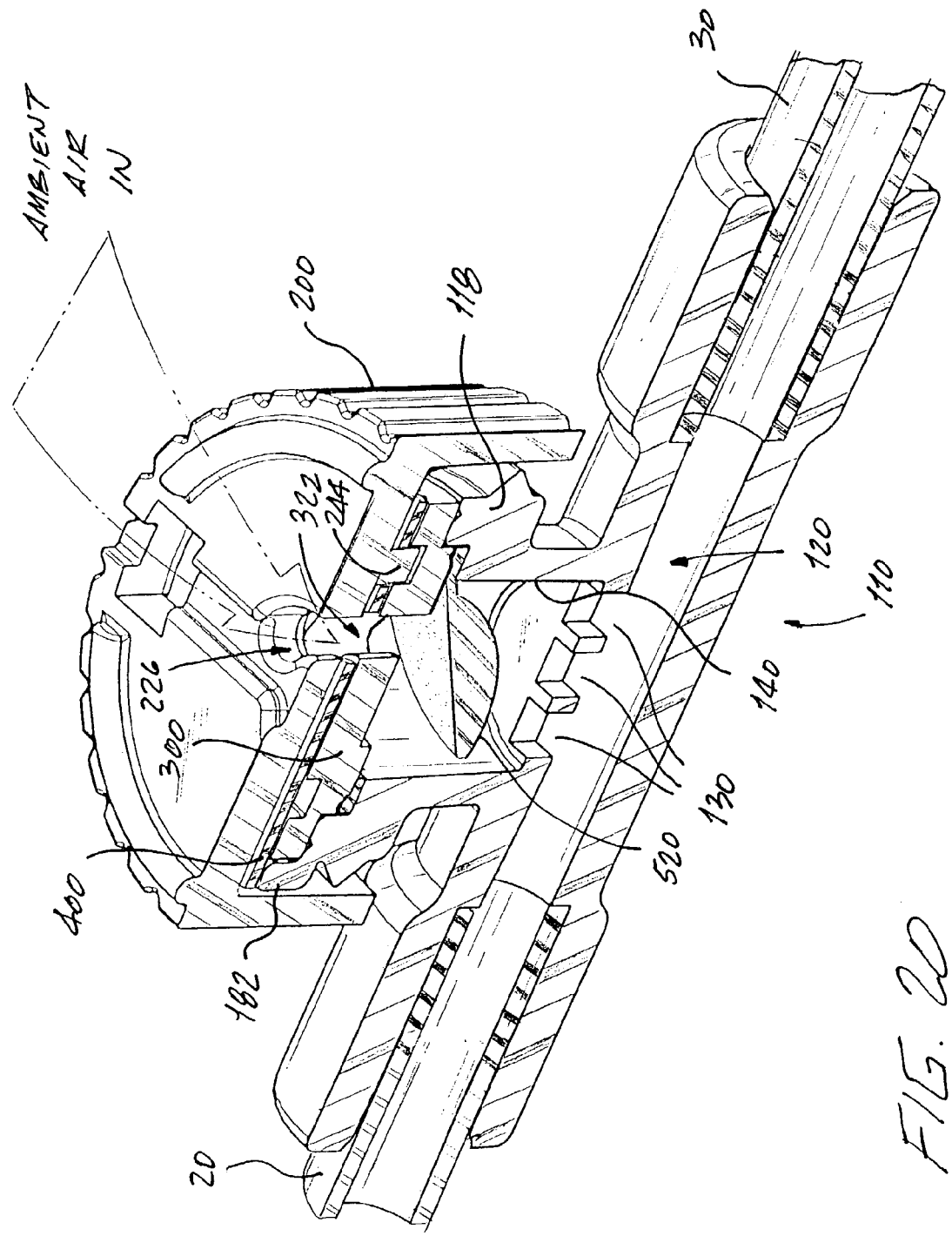
FIG. 20 is a cross-sectional view of the adjustable vent device connected to a pair of suction lines when a vacuum source is actuated.

For purpose of illustration and in reference to FIGS. 17–19, the main vent opening 322 of the present adjustable vent device 100 will be described as first being in the completely closed position; however, it will be clearly understood that the main vent opening 322 can initially be in any number of other different positions, including a completely open, or a partially open position. In this completely closed position, the vent opening 226 of the switch 200 is not in registration with the main vent opening 322 and when, the vacuum/suction system is activated and a vacuum (negative pressure) is applied to the main vent body 110, the gasket 400 is pulled downward over the main vent opening 322 to create the seal with the inner face 304 of the cap 300. Because the vent opening 422 formed in the gasket 400 is always aligned with the switch vent opening 226, a solid body section of the gasket 400 extends across and covers the main vent opening 322 of the cap 300, thereby preventing atmospheric air to communicate with the valve 500 and enter the vent housing 118. Accordingly, in the completely closed position, no airflow is allowed into the suction line from the atmosphere. The main vent opening 322, when in the closed position, allows the increase of fluid flow rate into the suction line 20, 30 from the patient.

It will also be appreciated that in the closed position, the valve 500 is open since it is acted upon by the negative pressure within the bore 120 of the main vent body 110. The valve 500 is exposed to the vacuum since the valve 500 seats at the top of vent housing 118 and the other end thereof includes ports 130 which provides fluid communication between the interior of the bore 120 and the interior of the vent housing 120. Thus, the applied vacuum exerts a force on the convex valve body 520 to cause the valve body 520 to hinge open by being drawn into the interior of vent housing 118. The design of the flapper valve 500 permits it to open even at low vacuum levels and conversely, when, and if, there is positive pressure in the suction line 20, 30, the valve 500 automatically closes.

The present adjustable vent device 100 is therefore constructed so that the valve 500 is not the air limiter of the system but rather the air limiter is the main vent opening 322 formed in the cap 300 and its relationship to the vent opening 226 formed in the switch 200. Instead, the purpose of the valve 500 is to prevent patient fluid and joint pressure from exiting through the main vent opening 322 since the valve automatically closes with any positive pressure in the interior of the main vent body 110 since this positive pressure is applied to the valve 500 to close it. Therefore, the valve 500 is only closed when positive pressure is applied from the inside. Otherwise, with suction applied, the valve 500 urges openly and the valve 500 automatically closes intermittently against intermittent positive pressure within the device 100. The valve 500 thus provides an extra safeguard to the device 100.

When suction is applied and the user rotates the switch 200 out of its completely closed position, the vent opening 226 and the main vent opening 322 begin to align and be in registration with each other, thereby providing a fluid flow of atmospheric air through the valve 500 and into the main vent body 110. The gasket 400 is still in the sealed positioned relative to the upper face 302 of the cap 300 and therefore, the size of the vent opening is defined by the amount of registration between the openings 226, 322. As the switch 200 is rotated toward the fully open position, there is increasingly more and more registration between the openings 226, 322 and this permits a greater airflow of atmospheric air into the suction line 20, 30, resulting in reduction in the vacuum (decrease in the negative pressure). Atmospheric air flows through the opening 226 and the gasket opening 422 and then through the portion of the main vent opening 322 that is in registration with the other openings, and then through the interior of the vent housing 118 and through the ports 130 into the bore 120.

As the user continues to rotate the switch 200 toward the fully open position, the overlap or registration between the opening 226 and the main vent opening 322 increases, thereby permitting a greater flow of atmospheric air into the system, which permits the user to control the degree of suction that is applied to the operative site. The rotation of the switch 200 thus does not open another path (as in some prior art devices) to expose another channel; but rather, it only causes alignment between the vent opening 226 formed therein and the controlled dimensioned main vent opening 322 in the cap 300. When the switch 200 is rotated to the completely open position, the openings 226 and 322 are in complete registration and the maximum atmospheric air flow is permitted into the suction line 20, 30. The vent mechanism of the device 100 is therefore constructed to permit fluid flow optimization and when the device 100 is added to an irrigation inflow system, it is designed to decrease the fluid outflow from the joint space so that the resultant joint pressure is better maintained under heavy outflowing conditions from surgical devices, such as high speed, large bore shavers.

The switch 200 provides the user with a means of closing off the main vent opening 322 of the cap 300, when needed, and leaving the device 100 in the "off" position, and not having to maintain a finger over a vent hole, to close off the vent. This is a vast improvement compared to the cumbersome vent devices of the prior art that required the user to maintain a finger over the vent hole to fully or partially restrict the vent hole. Moreover, the device 100, with its valve 500 and adjustable switch 200, can remain in place in the suction line 20, 30 and be open, as need be, throughout the entire surgical procedure regardless of whether the vacuum is applied or not. The inner diameter of the main vent opening 322 is not so great as to reduce the vacuum entirely, nor is it too small so as to not have any effect on the air flow and hence the fluid flow. The inner diameter of the main vent opening 322 is thus sized for fluid flow optimization. If the inner diameter were too large, it would result in insufficient fluid drawn from the patient since too much airflow could enter the suction line 20, 30. If the inner diameter were too small, it would result in ineffectual happenings, i.e., by not reducing the fluid flow out of the joint space enough to notice any appreciable difference in the resultant effects within the joint.

Figure 21:
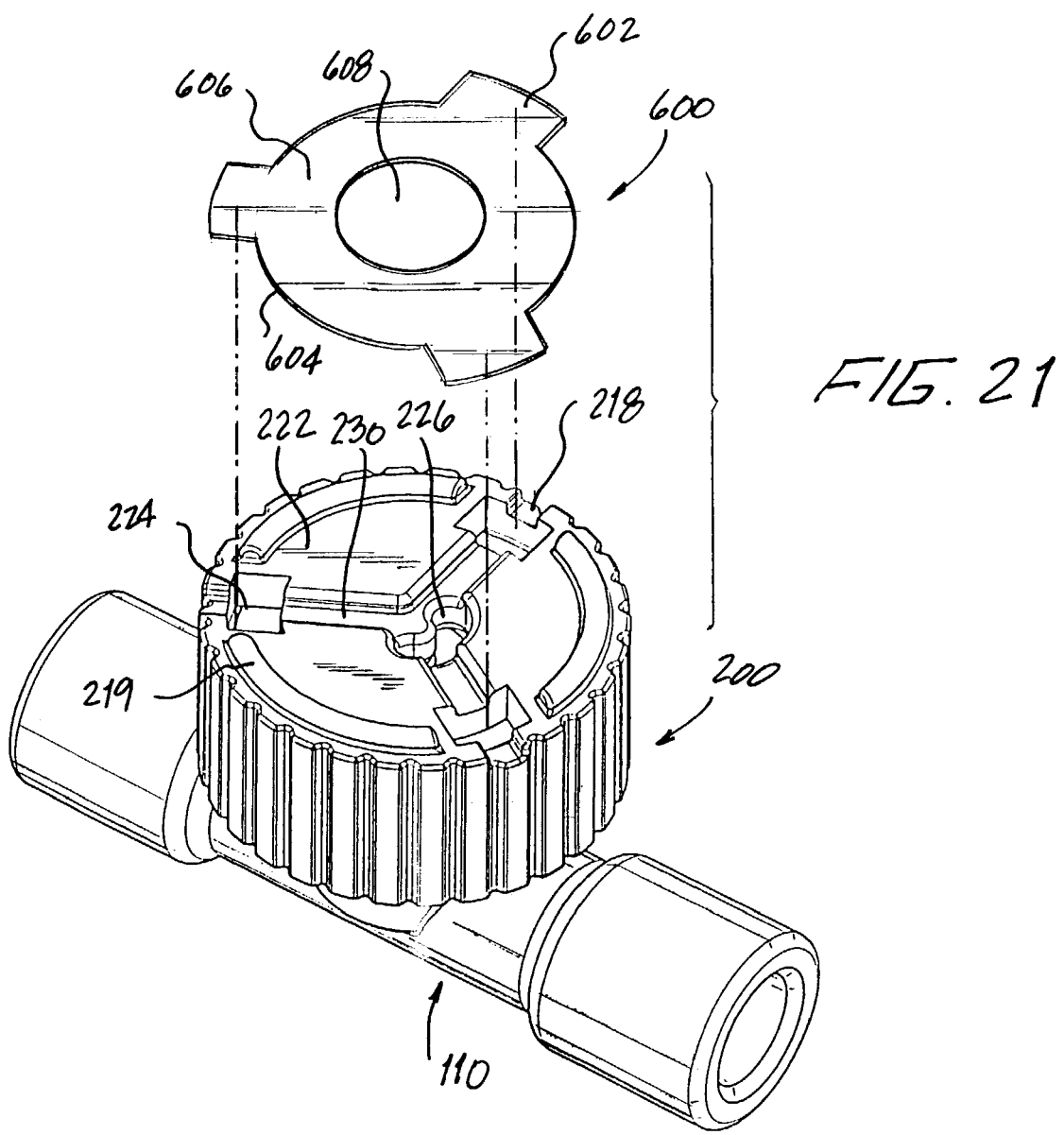
FIG. 21 is a perspective view of a label applied to the top of the switch.

Now referring to FIG. 21 in which the label or cover 600 is illustrated in exploded view relative to the switch 200. The label 600 is preferably formed of a plastic (polymeric) material and is generally circular in shape with the exception of radial tabs 602 that extend outwardly from a peripheral edge 604 of the label 600. The main body 606 of the label 600 is ring shaped as it is defined by the edge 604 and a central opening 608. The central opening 608 is positioned so that when the label 600 is disposed and securely attached to the outer surface 222 of the switch 200, the central opening 608 is disposed over the main opening 226 (kidney shaped opening). It will be understood that the central opening 608 has an area that is greater than an area of the main opening 226 so that the label 600 is not an impediment for air flow into and out of the main opening 226. In the illustrated embodiment, the central opening 608 is circular shaped.

The label 600 is disposed on the outer surface 222 such that each radial tab 602 extends to the outer edge of the cover wall 220 and in between two adjacent ribs 219. The tab 602 is constructed so that it completely covers one of the openings 224 and the main body 606 seals the channels 230 by acting as a ceiling that extends across the channels 230. Thus, the entrance to the secondary channels 230 is through the notches 218 and the air pathway extends to the main opening 226. The label 600 can be attached using a number of conventional techniques, including using an adhesive or using an ultrasonically welding process, etc. In another embodiment, the secondary channels 230 can be integrally molded in the top surface of the switch 200, including the "tops" of the channels.

It will further be understood that the device 100 is not intended to eliminate the use of any devices that are positioned distally on a patient, i.e., a Yankauer type device or a bulbous vented end, with distal side vent holes, whose purpose is to eliminate tissue from clogging the distal end of the suction device. Instead these types of devices and others can be used in combination with the device 100.

The present device is thus intended to be placed in line within the suction tubing after the shaver handpiece or other surgical instrument and before the suction line runs off the sterile field to the vacuum canister. The present device is designed to limit the outflow fluid flow and thus maintain joint pressure and distention and also, simultaneously, provides a device that when used in a closed system will allow the maximum pressure generated by the irrigation system to be transferred to the joint, without leakage through the proposed device. The device will limit the outflow fluid flow by relieving the full vacuum effect allowed to be transferred to the joint.

While this invention has been particularly shown and described with references to preferred embodiments thereof, it will be understood by those skilled in the art that various changes in form and details may be made therein without departing from the scope of the invention encompassed by the appended claims.

What is claimed is:

1. A suction limiting device with variable control for use in a surgical system, the device comprising:
 a main vent body having a fluid carrying bore extending therethrough from a first end to a second end;
 a variable vent mechanism having a main vent opening in selective fluid communication with the fluid carrying bore so as to permit introduction of atmospheric air into the fluid carrying bore, the vent mechanism being adjustable so that the degree of airflow into the fluid carrying bore is variable between a fully open position to a fully closed position where atmospheric air is prevented from entering the fluid carrying bore; and
 a valve disposed within the main vent body and positionable between an open position when negative pressure exists in the main vent body and a closed position when a positive pressure state exists in the main vent body, wherein in the closed position, the valve prevents fluid flow from the fluid carrying bore into the vent mechanism, wherein the vent mechanism includes:
 a cap member that has the main vent opening formed therethrough, the cap member being positioned relative to a vent housing section of the main vent body so that the main vent opening is the only entrance into the fluid carrying bore by passing through the vent housing section; and
 a switch that is rotatably and interlockingly coupled to the vent housing section with the cap member disposed between the switch and the vent housing section, the switch having a vent port formed therein, the switch being positioned between a fully open position where the vent port is in complete registration with the main vent opening and a fully closed position where the vent port is off set from the main vent opening.

2. The device of claim 1, wherein the main vent body has a first leg for connection to a surgical instrument and a second leg for connection to a vacuum source, which when activated draws fluid from the surgical instrument through the fluid carrying bore and towards the vacuum source, the main vent body having an intermediate body section between the first and second legs, the valve and the vent mechanism being associated with the intermediate body section.

3. The device of claim 2, wherein the intermediate section has a wall that defines an interior cavity which is in fluid communication with the fluid carrying bore through at least one fluid port and the intermediate section having a seat formed at a distal end of the wall for receiving the valve.

4. The device of claim 3, wherein the at least one fluid port is an opening formed in a cylindrical wall that defines the fluid carrying bore in the intermediate section.

5. The device of claim 3, wherein the seat is ring shaped with the interior cavity being formed therebetween.

6. The device of claim 3, wherein the seat is defined in part by an annular ring that has a diameter greater than a diameter of the interior cavity, the annular ring being formed above and integral to the wall that defines the interior cavity, the annular ring having a flange that extends outwardly therefrom along a circumferential length of the annular ring.

7. The device of claim 6, wherein the flange has an arcuate shape and is defined by first and second ends, an upper surface of the flange being flush with an upper surface of the annular ring.

8. The device of claim 6, further including: a rail formed along a length of the flange and extending upwardly from an upper surface of the flange, the length of the rail being less than a length of the flange.

9. The device of claim 2, wherein a diameter of the fluid carrying bore is less in the intermediate section than in each of the first and second legs.

10. The device of claim 1, wherein the cap member is disposed in a fixed position relative to the vent housing section and includes an inner face and an outer face, the inner face having a feature that seats within a recessed seat formed as part of the vent housing section for sealing a cavity of the vent housing section, the valve being disposed in the recessed seat below the feature.

11. The device of claim 10, wherein the outer face of the cap member has a recessed annular track formed therein and surrounding the main vent opening.

12. The device of claim 1, wherein the each of the main vent opening and the vent port has a kidney shape.

13. The device of claim 1, wherein the cap member is a substantially annular disk with an arcuate flange being forward circumferentially around a section thereof and a pair of spaced tabs protruding outwardly from a circumferential edge of the cap member.

14. The device of claim 13, wherein each of the spaced tabs is one of square shaped and rectangular shaped.

15. The device of claim 13, wherein the vent housing section has a wall that defines an interior cavity which is in fluid communication with the fluid carrying bore through at least one fluid port and the vent housing section has a seat formed at a distal end thereof for receiving the valve, the seat being defined in part by an annular ring that has a diameter greater than a diameter of the interior cavity, the annular ring having a flange that extends outwardly therefrom along a circumferential length of a section of the annular ring, wherein a rail is formed along a length of the flange and extending upwardly from an upper surface of the flange, the length of the rail being less than a length of the flange, the cap member disposed on an upper surface of the annular ring such that the rail is disposed between the pair of tabs to prevent rotation of the cap member relative to the vent housing section.

16. The device of claim 1, wherein the switch is a member that includes a cylindrical wall and an upper wall that extends across one end of the cylindrical wall so as to at least partially enclose the cylindrical wall, the vent port being formed through the upper wall.

17. The device of claim 16, wherein an outer surface of cylindrical wall has a plurality of vertical ribs formed thereon.

18. The device of claim 16, wherein the cylindrical wall has a plurality of notches formed therein at the end thereof where the upper wall is connected.

19. The device of claim 16, wherein the upper surface includes a plurality of air channels formed therein, one end of each channel forming an entrance into the vent port, while an opposite end of the channel forms an entrance into one notch.

20. The device of claim 19, further including a cover that is disposed on the upper surface so as to enclose the air channels such that air is permitted to enter the air channels only through the notches and flow to the vent port, the air channels acting as secondary air pathways.

21. The device of claim 20, wherein the cover is a flexible membrane that is securely attached to the outer surface, the cover having a central opening that is disposed over the vent port so that air freely flows through the cover and into and out of the vent port.

22. The device of claim 16, wherein an outer surface of the upper wall includes a plurality of rails formed thereon and extending outwardly therefrom.

23. The device of claim 16, wherein an inner surface of the upper wall includes a plurality of posts that extend outwardly therefrom.

24. The device of claim 16, wherein the plurality of posts includes at least three posts that are arranged around the vent port.

25. The device of claim 16, wherein an inner surface of the cylindrical wall includes a plurality of interlocking tabs that are formed at an end of the cylindrical wall opposite the upper wall.

26. The device of claim 1, wherein the vent mechanism includes a gasket that is coupled to the switch such that the position of the gasket relative to the switch is fixed when the switch is rotated, the gasket having a flexible body that includes a gasket opening that has a shape and dimensions substantially identical to the vent port.

27. The device of claim 26, wherein an inner surface of the switch includes a plurality of posts that extend outwardly therefrom, the gasket having apertures that receive the posts such that the gasket is slidable along the posts, wherein when negative pressure exists in the main vent body, the gasket seals against the cap member.

28. The device of claim 1, wherein the valve is a flapper valve.

29. The device of claim 1, wherein the valve comprises a flapper valve that includes a base ring that surrounds a valve body that is hingedly connected to the base ring, wherein application of negative pressure draws the valve body away from the base ring resulting in the opening of the valve.

30. The device of claim 1, wherein the valve comprises a flapper valve that includes a valve body that opens under application of negative pressure in the vent housing section, the valve being disposed underneath the cap member, wherein atmospheric air vents through the vent housing section through the open valve when the vent port and the main vent opening are in at least partial registration.

31. The device of claim 1, wherein the switch includes a first interlocking feature for detachably engaging a complementary second interlocking feature formed as part of the vent housing section in a snap fit manner.

32. The device of claim 27, wherein an outer surface of the cap member contains an annular track formed therein for receiving the posts of the switch to facilitate rotational movement of the switch.

* * * * *